US008888845B2

(12) United States Patent
Vaquero et al.

(10) Patent No.: US 8,888,845 B2
(45) Date of Patent: Nov. 18, 2014

(54) METHOD OF INSERTING AN INTRAOCULAR LENS

(75) Inventors: Edward A. Vaquero, Fairport, NY (US); Gary A. Richardson, Rochester, NY (US); Thomas M. Heyman, Placentia, CA (US)

(73) Assignee: Bausch & Lomb Incorporated, Rochester, NY (US)

(*) Notice: Subject to any disclaimer, the term of this patent is extended or adjusted under 35 U.S.C. 154(b) by 2143 days.

(21) Appl. No.: 11/584,024

(22) Filed: Oct. 20, 2006

(65) Prior Publication Data
US 2008/0097597 A1    Apr. 24, 2008

(51) Int. Cl.
A61F 2/16    (2006.01)

(52) U.S. Cl.
CPC ............ *A61F 2/1613* (2013.01); *A61F 2/1678* (2013.01); *A61F 2/1648* (2013.01)
USPC ....................................... 623/6.12

(58) Field of Classification Search
USPC ............. 623/6.12, 6.32–6.38, 6.11, 6.4, 6.39, 623/6.43, 5.14, 6.24; 606/107, 166
See application file for complete search history.

(56) References Cited

U.S. PATENT DOCUMENTS

| | | | |
|---|---|---|---|
| 4,681,102 A * | 7/1987 | Bartell | 606/1 |
| 4,842,601 A * | 6/1989 | Smith | 623/6.34 |
| 5,275,623 A | 1/1994 | Sarfarazi | |
| 5,474,562 A * | 12/1995 | Orchowski et al. | 606/107 |
| 6,197,058 B1 * | 3/2001 | Portney | 623/6.34 |
| 6,277,146 B1 * | 8/2001 | Peyman et al. | 623/6.17 |
| 6,336,932 B1 * | 1/2002 | Figueroa et al. | 606/107 |
| 6,423,094 B1 | 7/2002 | Sarfarazi | |
| 6,488,708 B2 | 12/2002 | Sarfarazi | |
| 6,607,537 B1 * | 8/2003 | Binder | 606/107 |
| 6,761,737 B2 | 7/2004 | Zadno-Azizi et al. | |
| 6,818,158 B2 * | 11/2004 | Pham et al. | 264/2.5 |
| 6,926,736 B2 * | 8/2005 | Peng et al. | 623/6.34 |
| 2003/0130732 A1 | 7/2003 | Sarfarazi | |
| 2004/0015236 A1 | 1/2004 | Sarfarazi | |
| 2005/0267575 A1 | 12/2005 | Nguyen et al. | |

* cited by examiner

*Primary Examiner* — Kathleen Holwerda
*Assistant Examiner* — Jocelin Tanner
(74) *Attorney, Agent, or Firm* — Toan P. Vo

(57) ABSTRACT

A method of folding a multiple element IOL comprising folding the first lens element and second lens element such that the second lens element at least partially surrounds the first lens element and such that, after folding, both the first lens element and the second lens element are substantially aligned along the optical axis. A hinged apparatus such as a cartridge may be used to cause the second lens element to be folded. A method of loading a multielement IOL comprising folding the haptics such that a portion of the haptics contacts an exterior side of one of the first lens element and the second lens element.

21 Claims, 22 Drawing Sheets

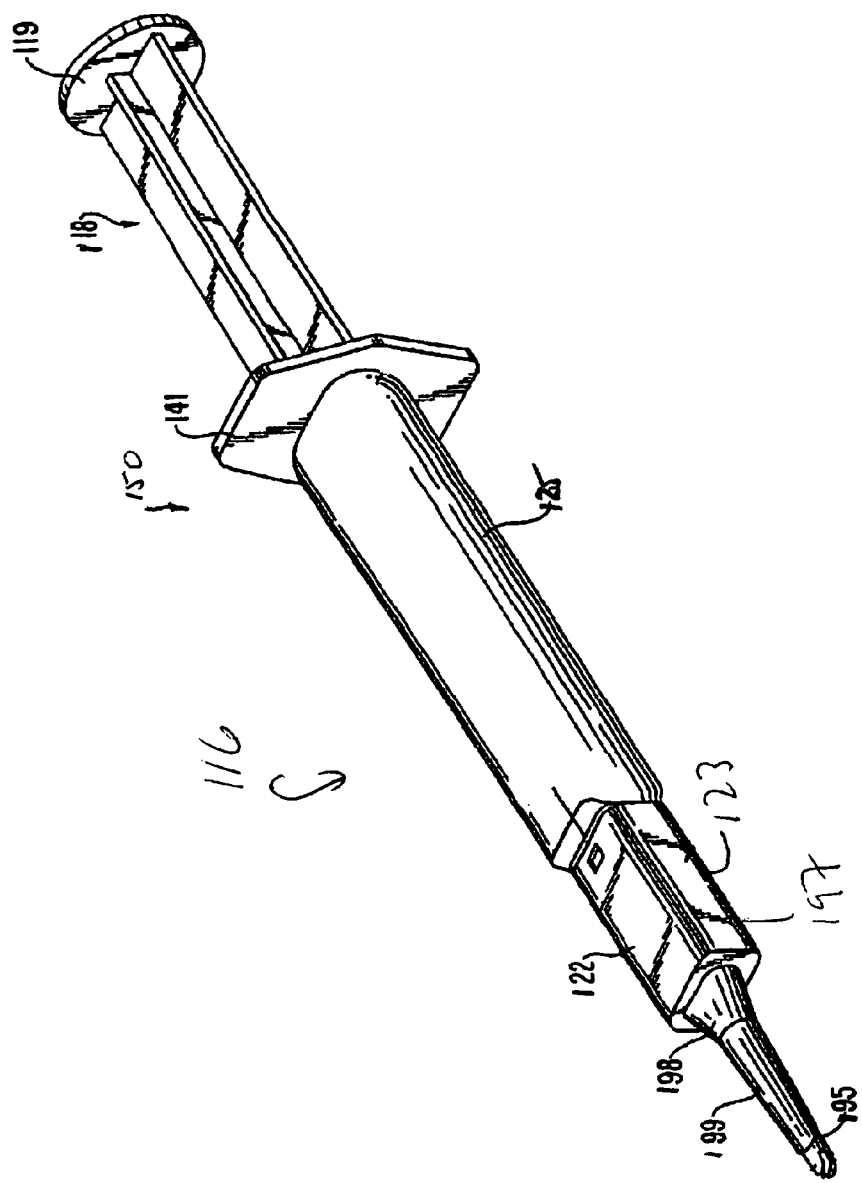

METHOD OF INSERTING AN INTRAOCULAR LENS

FIELD OF INVENTION

The present invention relates to a method of preparing an intraocular lens for insertion, and more particularly to a method of preparing a multielement intraocular lens for insertion.

BACKGROUND OF THE INVENTION

FIG. 1 illustrates a cross-sectional view of a human eye 10 having an anterior chamber 12 and a posterior chamber 14 separated by an iris 30. Within the posterior chamber 14 is a capsular bag 16 which holds the eye's natural crystalline lens 17. Light enters the eye by passing through cornea 18. The cornea and crystalline lens act together to direct and focus the light onto retina 20. The retina is connected to optic nerve 22 which transmits images received by the retina to the brain for interpretation. Eye 10 has a visual axis VA In response to the sharpness of the image received by the retina, the brain operates to contract or relax ciliary muscle 26. Ciliary muscle 26 is disposed within ciliary body 28, and upon contraction of the ciliary muscle, the ciliary body is caused to move. To achieve near-focus accommodation, the ciliary muscle is contracted thereby causing the ciliary body to relax tension on zonules 27 which permits the capsular bag and crystalline lens 17 to become more rounded. To achieve far focus (i.e., disaccommodation), the ciliary muscle is relaxed thereby increasing tension on zonules 27 which causes the capsular bag and crystalline lens 17 to become flatter.

In an eye where the natural crystalline lens has been damaged (e.g., clouded by cataracts), the natural lens is no longer able to properly focus and/or direct incoming light to the retina. As a result, images become blurred. A well known surgical technique to remedy this situation involves removal of a damaged crystalline lens. The lens is removed by first making an incision in the cornea, and then making a hole in the capsular bag known as a capsularhexis (also referred to simply as a rhexis). The crystalline lens is removed through the rhexsis and through the incision. Subsequently, an artificial lens known as an intraocular lens (IOL) can be placed into the evacuated capsular bag through incision and through the rhexis.

Conventional IOLs are typically fixed-focus lenses. Such lenses are usually selected to have a power such that the patient has a fixed focus for distance vision, and the patient requires spectacles or contact lenses to permit near vision. In recent years extensive research has been carried out to develop IOLs having variable focus capability. Such IOLs are known as accommodating IOLs (AIOLS). The term AIOLs refers to both single-element and multielement lens systems.

AIOLs permit a wearer to have accommodative vision. AIOLs are typically located in the posterior chamber (e.g., in the capsular bag) and provide variable focal power in accordance with tension or a lack of tension exerted on the capsular bag 16 as a result of contraction and relaxation of the ciliary muscle. FIG. 2 shows an example of two-element IOL 240 in capsular bag 16. IOL 240 comprises an anterior lens element 242 and a posterior lens element 244 that are connected to one another by haptics 246. The haptics permit lens elements 242 and 244 to translate relative to one another to achieve accommodation and disaccommodation. Further details of IOL 240 are given in U.S. Pat. No. 6,488,708 issued Dec. 3, 2002, to Sarfarazi. The substance of said patent is hereby incorporated by reference. In some embodiments, of IOL 40, anterior lens element diameter and the posterior lens element diameter are approximately 5.5 mm and the overall diameter of the lens (including the haptics is approximately 9.3 mm).

To date, although there have been numerous patent filings directed to multielement AIOLs, there have been few filings related to insertion techniques for delivering such AIOL into an eye. Furthermore, those techniques that have been described to date, which include an injector device, have required substantially completely newly designed for implanting AIOLs into patients' eyes.

In addition to multielement AIOLs, multielement non-accommodative IOLs have been proposed. Similar to AIOLs, there have been few filings related to insertion techniques for delivering such multielement IOLs into an eye.

SUMMARY

Aspects of the present invention are directed to folding techniques for use in reducing the cross-sectional shape of multielement IOLs (i.e., accommodative and non-accommodative IOLs) for insertion into an eye. Other aspects of the present invention are directed to techniques for loading an IOL inserter with a multielement IOL for subsequent insertion into an eye.

A first aspect of the invention is directed to a method of folding a multiple element IOL comprising a first lens element and a second lens element that are aligned along an optical axis, the method comprising folding the first lens element and the second lens element such that the second lens element at least partially surrounds the first lens element and such that, after folding, both the first lens element and the second lens element are substantially aligned along the optical axis.

In some embodiments, after the step of folding, the first lens element is folded such that outer portions of the first lens element are displaced towards the second lens element. In other embodiments, after the step of folding, the first lens element is folded such that outer portions of the first lens element are displaced away from the second lens element.

In some embodiments, after said step of folding, the second lens element is configured to form a single concavity in which the first lens element is disposed. In some embodiments, the step of folding the first lens element and the second lens element comprises steps of (1) folding the first lens element; and (2) folding the second lens element such that the second lens element at least partially surrounds the first lens element. In some embodiments, the step of folding the first lens element occurs prior to the step of folding the second lens element.

The step of folding the first lens element may comprise folding the first lens element substantially along its centerline. The step of folding the second lens element may comprise folding the second lens element substantially along its centerline.

In some embodiments, the first lens element is an anterior lens element and the second lens element is a posterior lens element. In other embodiments, the first lens element is a posterior lens element and the second lens element is an anterior lens element. In some embodiments, the second lens element is more massive than the first lens element. In some embodiments, after the step of folding, at least a portion of an interior surface of the second lens element contacts at least a portion of an exterior surface of said first lens element.

In some embodiments, the step of folding the second lens element may comprise (1) locating the second lens element on a hinged apparatus, the hinged apparatus comprising a first portion and a second portion, the first portion being connected to the second portion by a hinge; and (2) rotating the first portion relative to the second portion. The method may comprise loading the hinged apparatus into an IOL inserter while maintaining the IOL in the hinged apparatus.

In some embodiments, the method further comprises actuating the IOL inserter to insert the IOL into an eye. In some embodiments, the step of actuating the IOL inserter results in compression of the IOL prior to insertion in the eye.

Another aspect of the invention is directed to a method of facilitating loading an IOL inserter with an IOL comprising a first lens element and a second lens element that are aligned along an optical axis, the method comprising (1) locating the second lens element on a hinged apparatus having a first portion and a second portion coupled together by a hinge, and (2) rotating the first portion relative to the second portion to cause the second lens element to be folded such that the second lens element at least partially surrounds the first lens element and such that, after folding, both the first lens element and the second lens element are substantially aligned along the optical axis.

The method may further comprise folding the first lens element, prior to the step of locating the second lens element. In some embodiments, the step of folding the first lens element may comprise folding the first lens element such that outer portions of the first lens element are displaced towards the second lens element. In other embodiments, the step of folding the first lens element comprises folding the first lens element such that outer portions of the first lens element are displaced towards the second lens element.

In some embodiments, the first lens element is an anterior lens element and the second lens element is a posterior lens element. In other embodiments, the first lens element is a posterior lens element and the second lens element is an anterior lens element. In some embodiments, the second lens element is more massive than the first lens element.

In some embodiments, after said step of rotating, at least a portion of an interior surface of the second lens element contacts at least a portion of an exterior surface of said first lens element. In some embodiments, the method further comprises loading the hinged apparatus into an IOL inserter while maintaining the IOL in the hinged apparatus.

In some embodiments, the method further comprises actuating the IOL inserter to insert the IOL into an eye. In some embodiments, the step of actuating the IOL inserter results in compression of the IOL prior to insertion in the eye.

Yet another aspect of the invention is directed to a method of facilitating loading an IOL inserter with an IOL comprising a first lens element and a second lens element that are aligned along an optical axis, the method comprising (1) locating the second lens element on a hingeless cartridge, the cartridge comprising a lumen, and (2) pushing the IOL along the lumen to cause the second lens element to be folded such that the second lens element at least partially surrounds the first lens element and such that, after folding, both the first lens element and the second lens element are substantially aligned along the optical axis.

In some embodiments, the method further comprises folding the first lens element, prior to the step of locating the second lens element. In some embodiments, the step of folding the first lens element comprises folding the first lens element such that outer portions of the first lens element are displaced towards the second lens element. In other embodiments, the step of folding the first lens element comprises folding the first lens element such that outer portions of the first lens element are displaced away from the second lens element.

In some embodiments, the first lens element is an anterior lens element and the second lens element is a posterior lens element. In other embodiments, the first lens element is a posterior lens element and the second lens element is an anterior lens element

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIG. 17A and 17B illustrate of further details of the inserter of FIG. 15;

DETAILED DESCRIPTION

Figure 1:
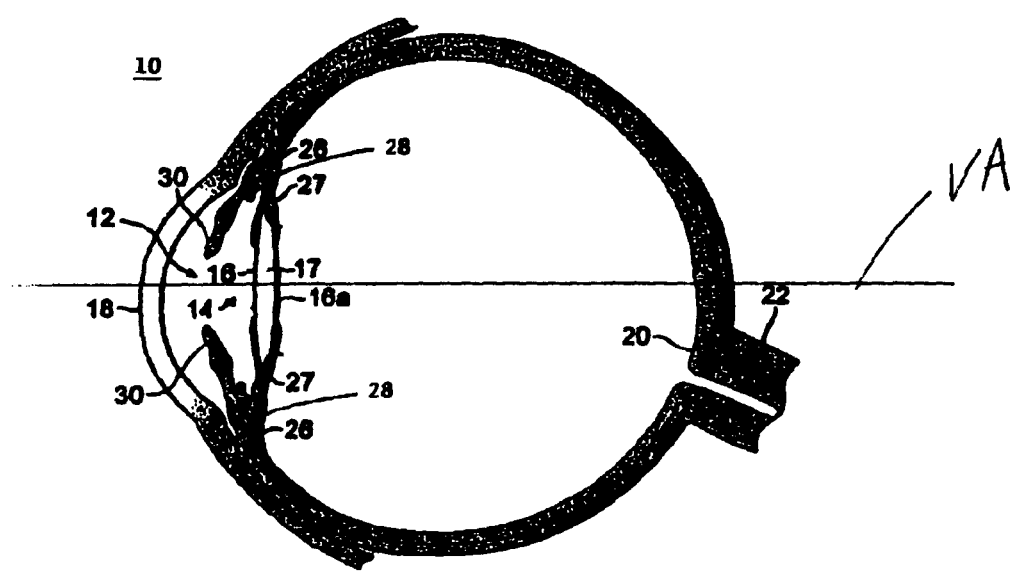
FIG. 1 illustrates a cross-sectional view of a human eye.
Figure 2:
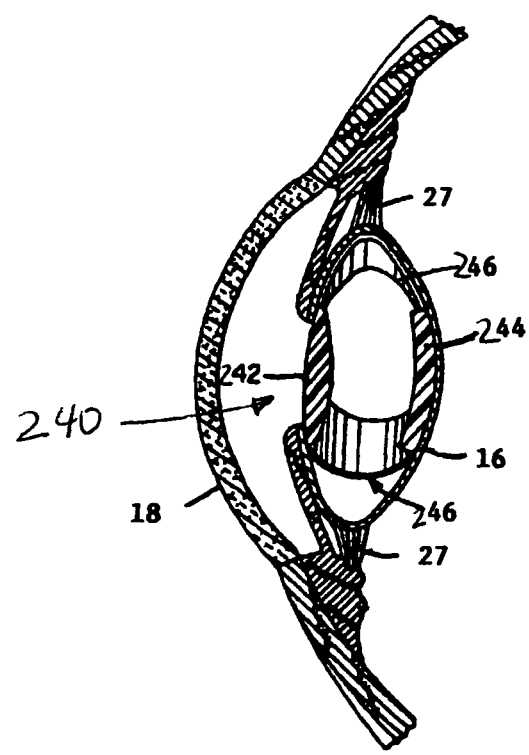
FIG. 2 illustrates an example of a conventional two-element AIOL in a capsular bag.
Figure 3:
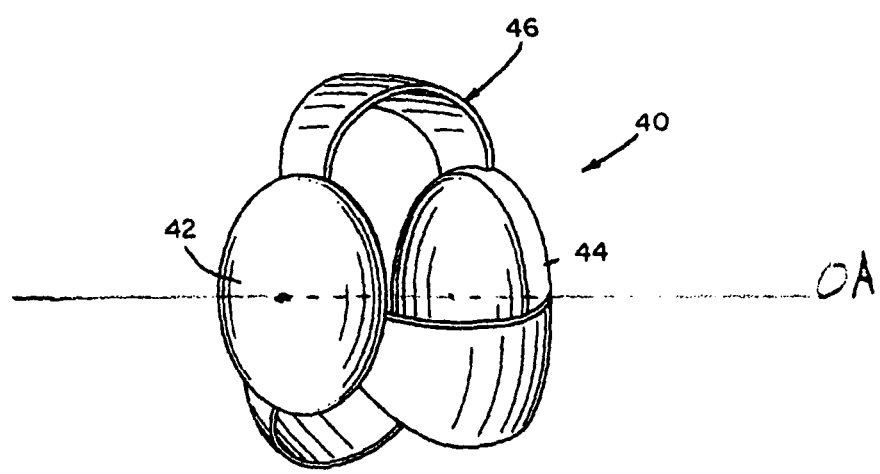
FIG. 3 illustrates the two-element AIOL in FIG. 2 in greater detail.

FIG. 3 shows an example of a two-element IOL such as the IOL illustrated in FIG. 2. IOL 40 is a multielement IOL comprising a first lens element 42 and a second lens element 44 that are connected to one another by haptics 46. The first lens element and a second lens element are aligned along an optical axis OA. Suitable IOLs for use with aspects of the present invention are made of a flexible material such as silicone, hydrogel or soft acrylic. The term "first lens element" may refer to either an anterior lens element or a posterior lens element of an IOL; and the term "second lens element" refers to the other of the anterior lens element and the posterior lens element.

Figure 4A:
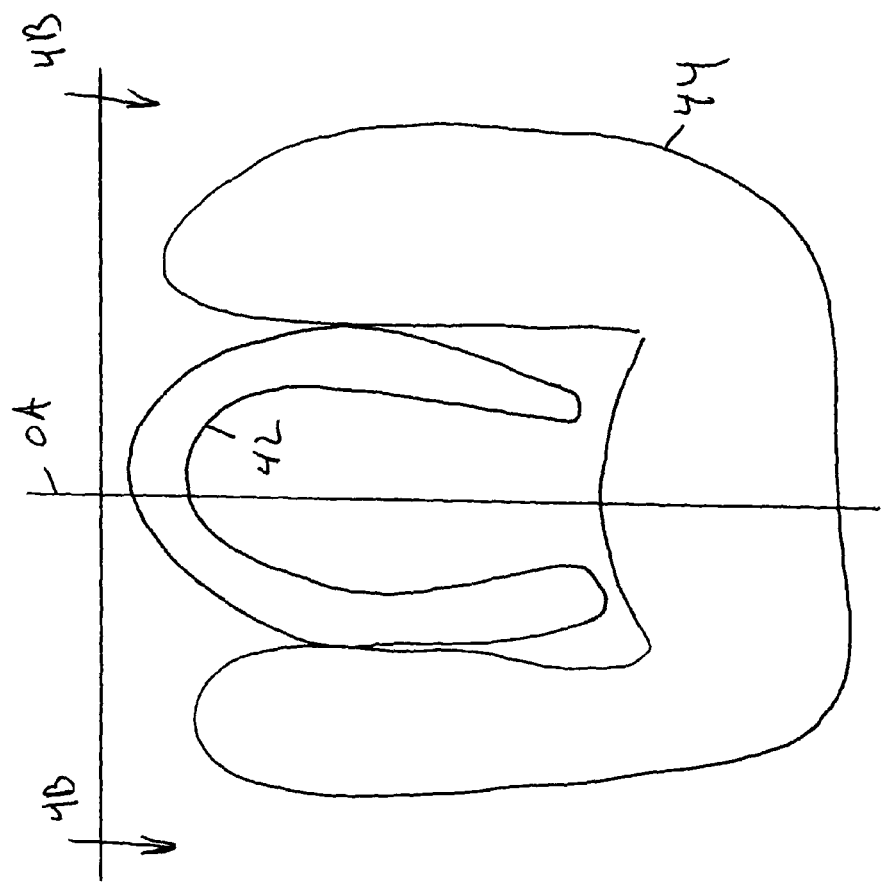
FIG. 4A is a side view of the first lens element and second lens element folded such that the second lens element at least partially surrounds the first lens element.
Figure 4B:
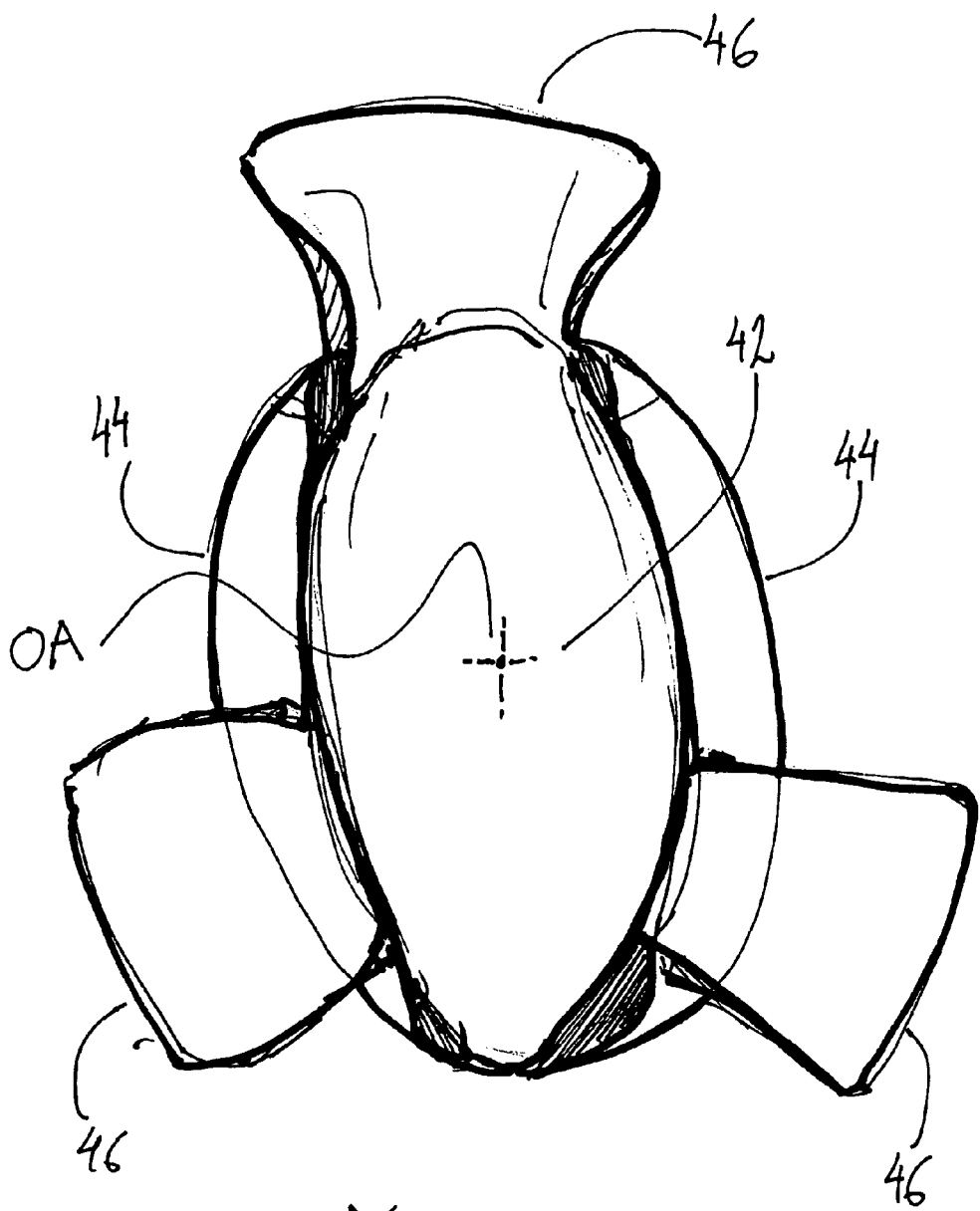
FIG. 4B is a top view of the first lens element and second lens element folded such that the second lens element at least partially surrounds the first lens element.

FIG. 4A illustrates the first lens element 42 and second lens element 44 being in a folded state such that second lens element 44 at least partially surrounds first lens element 42. FIG. 4B is a top view of first lens element 42 and second lens element 44 viewed along lines 4B-4B of FIG. 4A. FIGS. 4A and 4B further illustrate that, after folding, both the second lens element and the first lens element remain substantially aligned along the optical axis OA. The term "folding" as used herein means bending to achieve a stressed state.

Figure 5A:
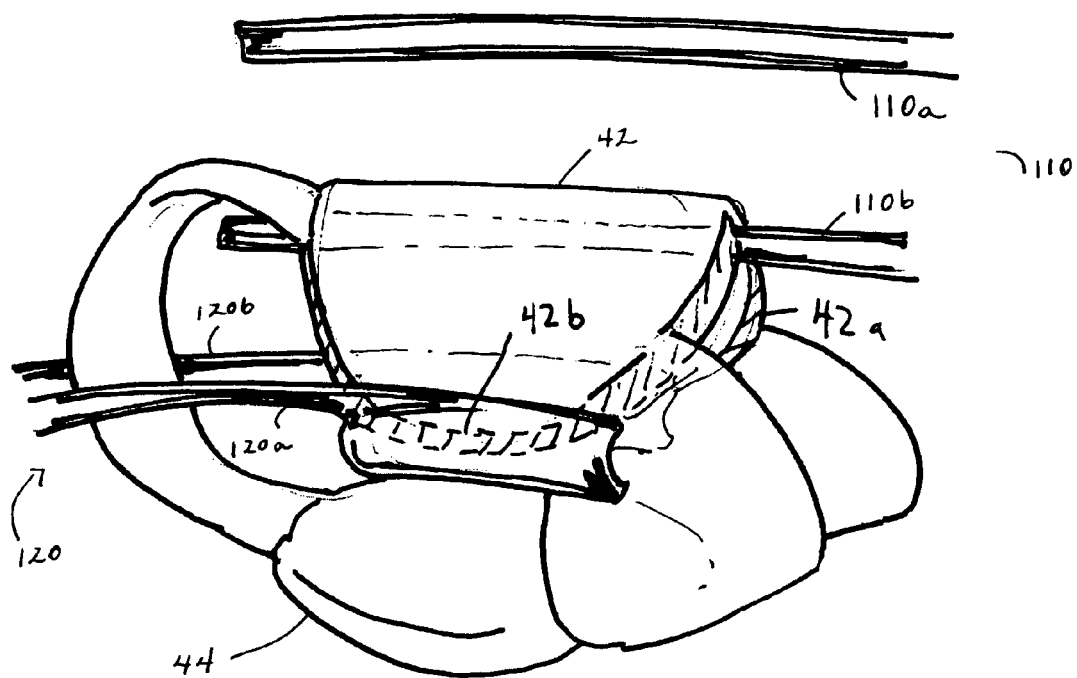
FIGS. 5A, 5B, 6 and 7 illustrate an example of a technique for achieving a folded IOL as illustrated in FIG. 4.
Figure 5B:
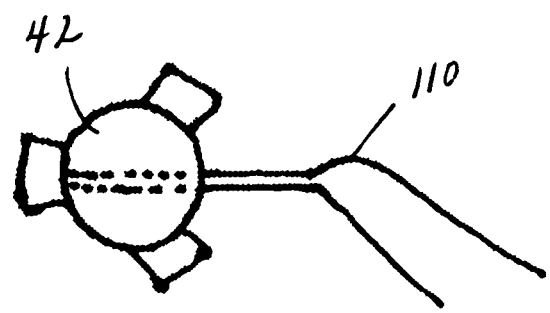

FIGS. 5A, 5B, 6 and 7 illustrate an example of techniques for achieving a folded IOL as illustrated in FIG. 4. As illustrated in FIG. 5A, according to some techniques first lens element 42 is manipulated along a centerline (i.e., a diameter) by an arm 110b of a first forceps 110. FIG. 5B is a top view that illustrates forceps 110 manipulating first lens element 42. It will be appreciated that forceps 110 in FIGS. 5A and 5B are only partially illustrated.

Subsequently, also as illustrated in FIG. 5A, a second forceps 120 is used to grasp first lens element 42 along its outer surface to fold lens element 42 substantially about the centerline. That is to say, first lens element 42 is folded such that outer portions 42a and 42b of the first lens element are displaced towards the second lens element 44.

It is to be appreciated that although folding of the first lens element is illustrated as occurring with the use of two forceps, in other embodiments, folding may be achieved by the use of human hands without forceps, or with tweezers or with any other suitably configured apparatus. In some embodiments, folding can be achieved using a combination of any of forceps, fingers or tweezers.

Figure 6:
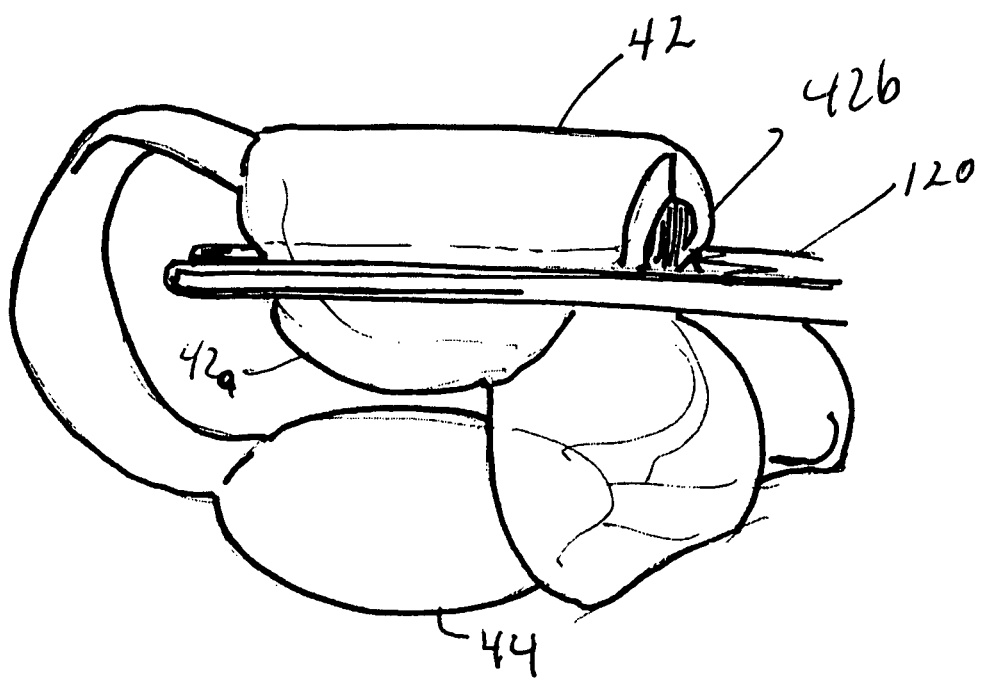

FIG. 6 illustrates that, after folding the first lens element 42, first forceps 110 can be removed. First lens element 42 is maintained in a folded configuration by second forceps 120.

Figure 7:
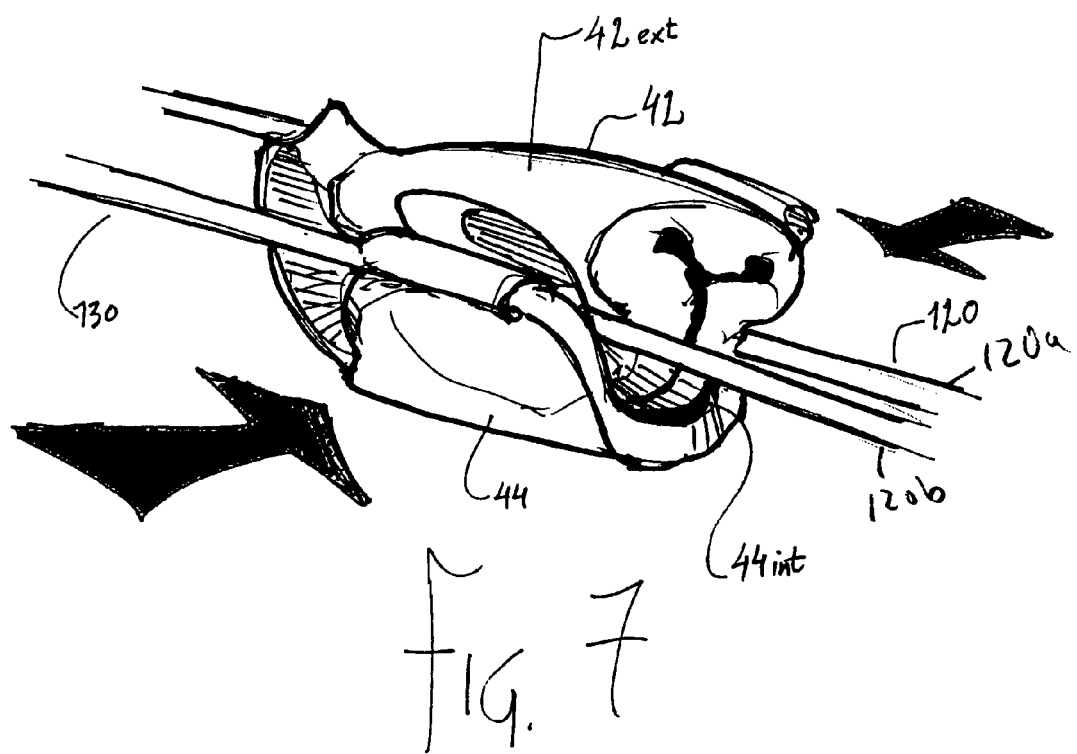

FIG. 7 illustrates the second lens element 44 being folded by a third forceps 130 such that the second lens element at least partially surrounds the first lens element. In the illustrated embodiment, the interior side 44int of the second lens element 44 (i.e., the side facing toward first lens element 42 when the lens is in an unstressed state) contacts the exterior side 42ext (i.e., the side facing away from first lens element 42 when the lens is in an unstressed state) of first lens element 42. It will be appreciated that after folding the second lens element, both the second lens element and the first lens element remain substantially aligned along the optical axis OA. In some instances, as illustrated, the second lens element 44 forms a single concavity in which the first lens element is disposed. In other instances, second lens element 44 at least partially surrounds first lens element 42 while taking a more complex shape.

It will also be appreciated that, after folding the second lens element such that the second lens element at least partially surrounds the first lens element, IOL 40 is substantially reduced in profile, such that the IOL can be inserted into a much smaller corneal incision than if the IOL were not so folded. According to one technique, forceps 120 can be removed after lens element 44 is folded; the first lens element 42 and the second lens element 44 are maintained in a folded state with forceps 130. Forceps 130 may then be used to inserter the IOL into an eye.

In some embodiments, the posterior lens element can be folded first (i.e., the posterior lens element is the second lens element 44). In such embodiments, the anterior lens element is folded such that it at least partially surrounds the posterior lens element. In other embodiments, the anterior lens element can be folded first (i.e., the anterior lens element is the second lens element.) In such embodiments, the posterior lens element will be folded such that it at least partially surrounds the posterior lens element. In some embodiments, it is advantageous to fold the less massive lens element first and to fold the more massive lens element so as to at least partially surround the less massive lens element.

Figures 8A, 8B:
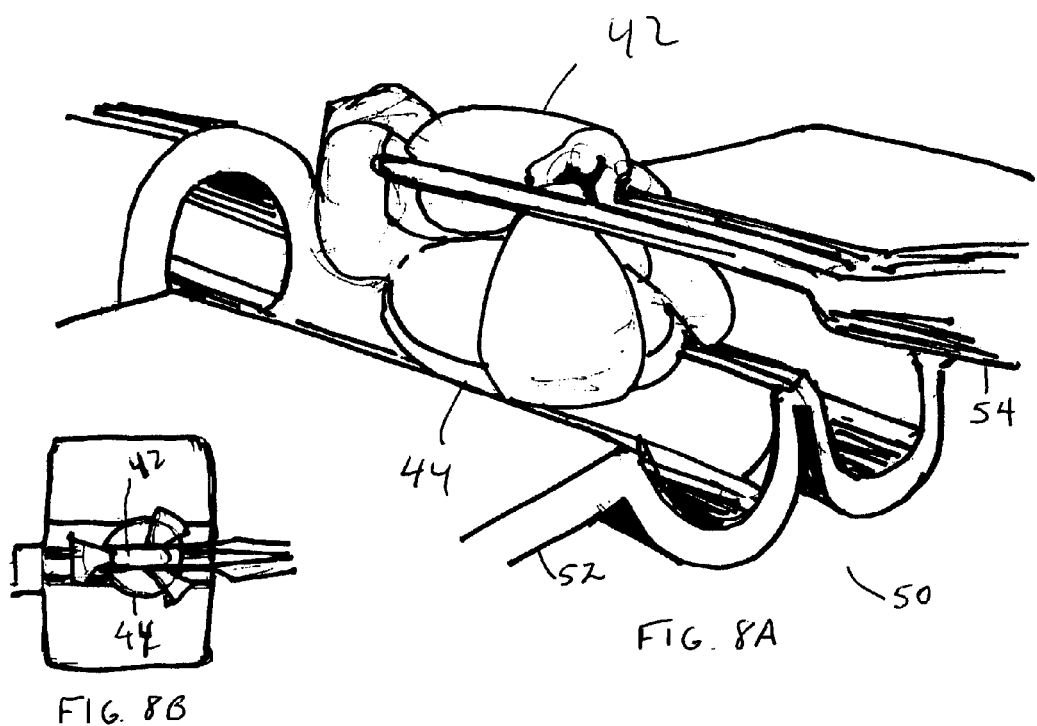
FIGS. 8A, 8B and 9 illustrate an alternative technique for achieving a folded IOL as illustrated in FIG. 4.
Figure 9:
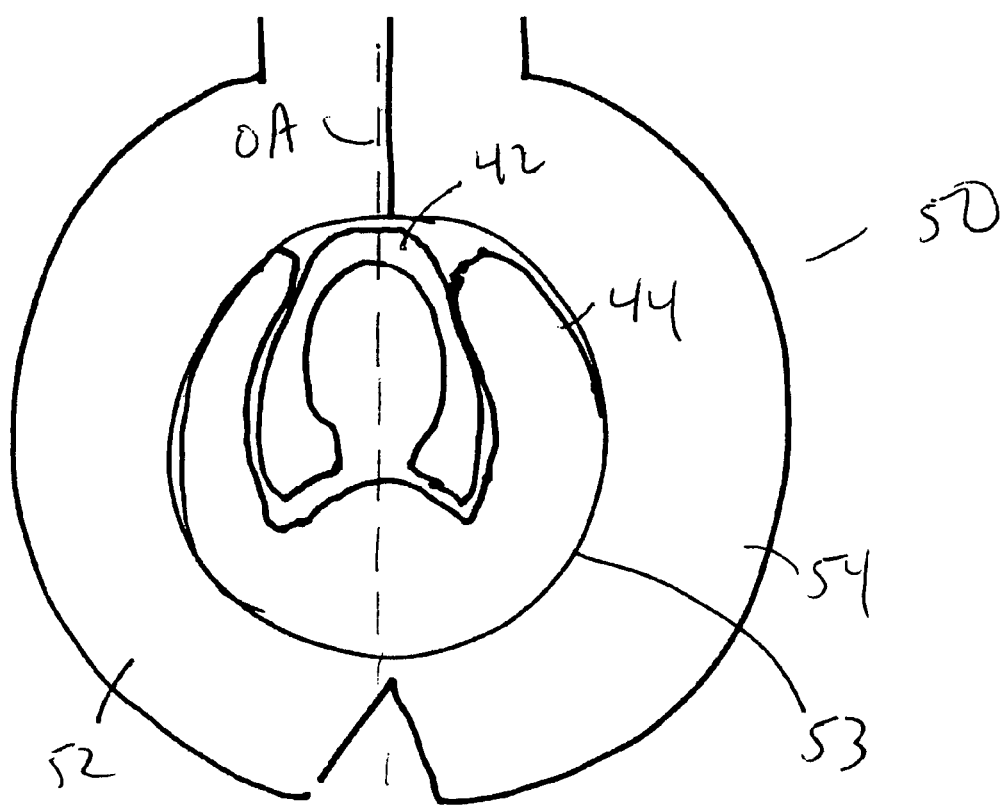

FIGS. 8A, 8B and 9 illustrate an alternative technique for achieving a folded IOL as illustrated in FIG. 4A. According to the alternative technique, the first lens element may be folded in any manner as described above with reference to FIGS. 5A, 5B and 6 (e.g., using forceps, tweezers or hands). And, FIGS. 8A, 8B and 9 illustrate folding the second lens element using a hinged apparatus 50.

As illustrated in FIG. 8A, in some embodiments, the second lens element 44 is placed on the hinged apparatus with the hinge substantially aligned with a centerline of the second lens element. FIG. 8B is a top view of the IOL located on the hinged apparatus. As illustrated in FIG. 9, by rotating a first portion 52 of the hinged apparatus relative to a second portion 54 of the hinged apparatus, the second lens element is folded such that the second lens element at least partially surrounds the first lens element 42. In the illustrated embodiment, after relative rotation of the portions, a lumen 53 is formed in which the IOL is located. It will be appreciated that after folding the second lens element, both the second lens element and the first lens element remain substantially aligned along the optical axis OA.

In some instances, upon closing hinged apparatus 50 of the illustrated embodiment, a portion of the first lens element and/or the haptics may become trapped between portions 52 and 54 of the hinged apparatus. In such instances, a forceps or other suitable device may be used to press the first lens element and/or haptics into the lumen.

It will be appreciated that after folding the second lens element such that the second lens element is at least partially surrounds first lens element, the IOL 40 is substantially reduced in profile, such that the IOL can be inserted into a much smaller corneal incision and/or rhexis than if the IOL were not so folded. As discussed above, the first lens element can be the anterior lens element or the posterior lens element, and the other of the anterior lens element and posterior lens element is the second lens element.

Hinged apparatus 50 may be any suitable hinged apparatus. For example, the hinged apparatus may be a conventional IOL inserter cartridge. In some embodiments, the cartridge may be a winged cartridge. In embodiments where the hinged apparatus is a cartridge, after closing of the cartridge, the lumen may be aligned with the lumen of the injector (not shown) and the IOL inserted into a patient's eye by actuating a plunger (not shown). In some embodiments, the lumen of the inserter may be tapered such that the IOL is further compressed as the IOL is pushed along the lumen by the plunger into the eye.

In some embodiments, the hinged apparatus may be a holder/folder apparatus. In such embodiments, the IOL may be removed from the holder/folder apparatus after folding and then located in an appropriate injector device or directly into a patient's eye using forceps.

An advantage of the folding techniques discussed above is that contact between the surfaces of the first lens element and the second lens element is limited; and the folding of the lenses provides substantial potential energy, such that when the IOL is released from its folded (i.e., stressed) state, the first lens element and the second lens element readily separate from one another. That is, they overcome any cohesion between the lenses and readily attain an unstressed state.

Figure 24:
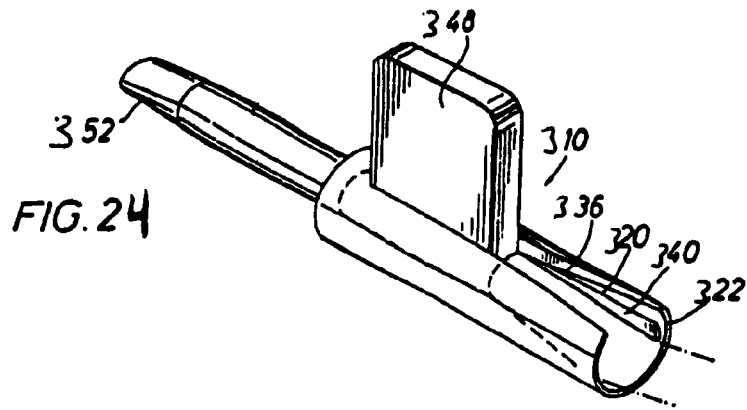
FIGS. 24-26 illustrate an example of a hingeless, rear-loaded cartridge suitable for use in practicing aspects of the present invention.

Although a winged cartridge was discussed above, other types of cartridges may be used. For example, a cartridge may be a hingeless, rear-loaded cartridge, such as cartridge 310 shown in FIGS. 24-26. The cartridge may be used to achieve a folded IOL in which the first lens element 42 and second lens element 44 are folded such that second lens element 44 at least partially surrounds first lens element 42, and such that, after folding, both the second lens element and the first lens element remain substantially aligned along the optical axis OA (as shown in FIG. 26).

According to some techniques, loading of IOL 40 into cartridge 310 is performed with forceps 120. According to one example of a loading technique, forceps 120 can be used to grasp the first lens element 42 as shown in FIG. 6 (i.e., the first lens element is folded such that outer portions of the first lens element are displaced towards the second lens element) before the IOL is loaded into the cartridge in the manner described below. The arms 120a and 120b of the forceps are preferably long enough so that they can grip the IOL 40 as shown and push it through the loading area 320 and into a staging area 334.

Before the IOL 40 is inserted into cartridge 310, the loading area is typically lubricated by depositing an amount of viscoelastic. The loading area 320 comprises a passageway which is cylindrical in cross section (or other appropriate shape) and gradually decreases in diameter in the direction of tip 352. In some embodiments, the loading area 320 is formed with a slot 336 so that once the IOL is inserted in the staging area 334, the forceps can easily be withdrawn. According to some techniques, the IOL may be inserted loading area through slot 336.

Figure 25:
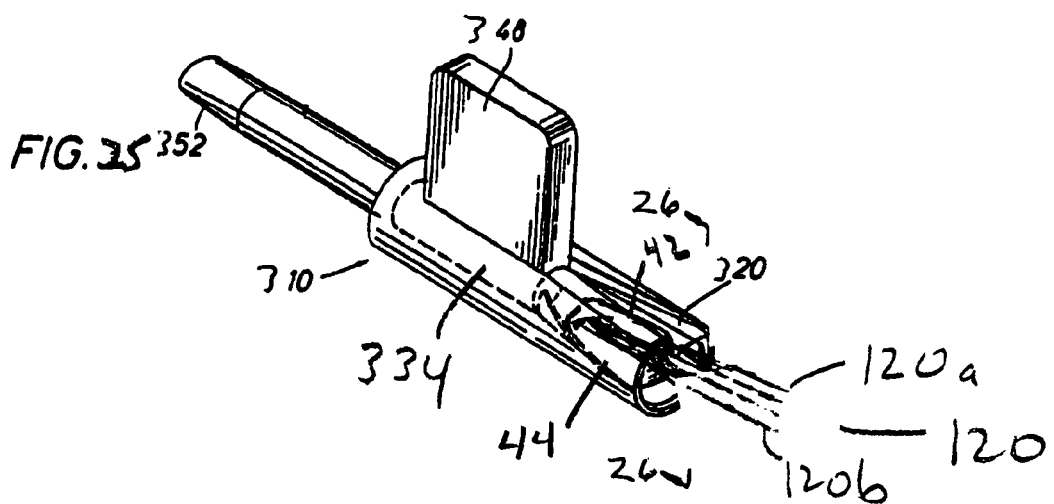
Figure 26:
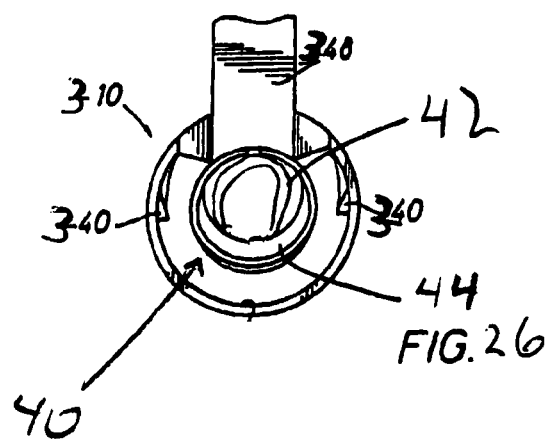

As shown in FIG. 25, the IOL is inserted directly into the proximal end 322 of the loading area 320. As the IOL is pushed toward the staging area 334, the walls which define the loading area operate to cause the edges of second lens element 44 to curl upwardly. As the IOL is pushed toward the staging area 334, the diminishing-diameter surface of the loading area 320 causes second lens element 44 to deform and compress while the first lens element 42 is held by the forceps. Accordingly, the IOL is deformed from the shape shown in FIG. 6, to a shape as shown in FIG. 26.

A pair of ridges 340 may be formed on the inner surface of at least a portion of the length of the walls which define the loading area 320 for guiding the outer edges of second lens element 44. In some embodiments, the edges of the second lens element are inserted beneath the ridges 340. As shown, in particular in FIG. 24, the ridges move upwardly along the surface of the wall which defines the loading area 320 for guiding the edges of the second lens element 44 into their curled position until they reach the staging area 334.

The staging area 334 is formed with a passageway that operates as a continuation of the passageway in the loading area 320. In some embodiments, the staging area passageway also gradually diminishes in size along its length. After the IOL 40 is loaded in the cartridge as described and shown, the lumen may be aligned with the lumen of an injector (not shown) using handle 348. Subsequently, the IOL can be pushed through tip 352 and inserted into a patient's eye by actuating a plunger (not shown). It is to be appreciated that, in some embodiments, the first lens element and the second lens element are maintained on the optical axis throughout the loading and insertion process.

U.S. Pat. No. 6,214,015 issued Apr. 10, 2001 to Reich, et al. includes further details of a rear-loaded cartridge that may be used to fold a multielement IOL according to aspects of the present invention. The substance of said patent is hereby incorporated by reference.

Figure 11:
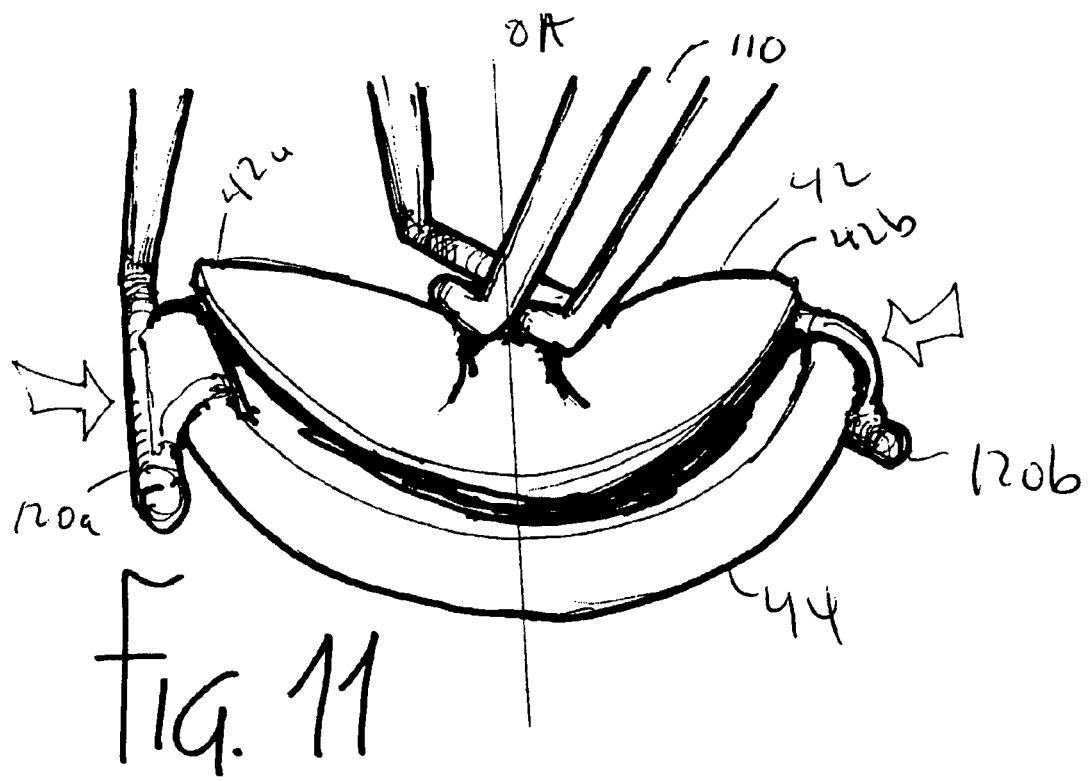

Although the technique described above included folding the first lens element such that outer portions of the first lens element are displaced towards the second lens element prior to loading the AIOL into the cartridge in other embodiments, according to other techniques, the first lens element may be folded such that outer portions of the first lens element are displaced away from the second lens element prior to loading the AIOL into the cartridge (in the manner shown in FIG. 11).

In a manner similar to what was described above, the IOL is then inserted directly into the proximal end 322 of the loading area 320. As the IOL is pushed toward the staging area 334, the walls which define the loading area operate to cause the edges of second lens element 44 to curl upwardly. As the IOL is pushed toward the staging area 334, the diminishing-diameter surface of the loading area 320 causes second lens element 44 to deform and compress while the first lens element 42 is held by the forceps.

Figure 10:
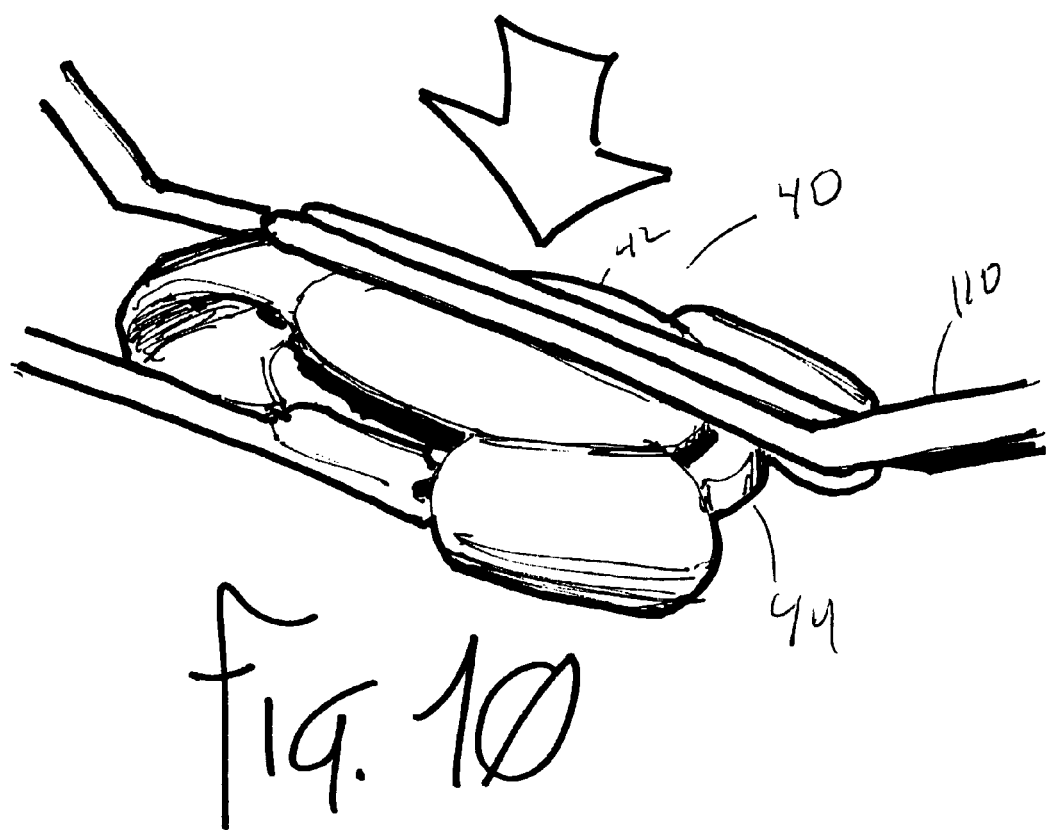
FIGS. 10 and 11 illustrate an alternative technique for folding the first lens element and second lens element such that the second lens element at least partially surrounds the first lens element.

FIG. 10 illustrates a first step in an alternative technique for folding multielement IOL 40. In the illustrated embodiment, the first lens element 42 and second lens element 44 are folded such that the second lens element at least partially surrounds the first lens element and such that, after folding, both the second lens element and the first lens element remain substantially aligned along the optical axis OA.

In FIG. 10, first lens element 42 and second lens element 44 are pressed toward one another by first forceps 110. As illustrated in FIG. 11, a second forceps 120 (i.e., arms 120a and 120b) is then used to grasp the outer edges of second lens element 44 and to fold the second lens element. The first lens element 42 is caused to fold by the folding of the second lens element 44. It will be appreciated that in the illustrated embodiment, the step of folding the second lens element and first lens element comprises folding the second lens element such that the second lens element at least partially surrounds the first lens element and such that outer portions 42a, 42b of the first lens element 42 are displaced away from the second lens element 44. The first lens element may be an anterior lens element or a posterior lens element.

In some embodiments, the step of pressing the first lens element 42 and second lens element 44 toward one another is performed with the second lens element being disposed on a cartridge (see hinged apparatus 50 illustrated in FIG. 8A). The subsequent step of folding the first lens element and the second lens element can be achieved by closing the cartridge. Although, in the illustrated embodiment, in some embodiments, the first lens element is caused to fold by folding the second lens element around the first lens element, the first lens element and the second lens element may be folded independently (e.g., by first folding the first lens element and then folding the second lens element such that is at least partially surrounds the first lens element).

It is to be appreciated that although folding is illustrated as occurring with the use of a forceps and a cartridge, in other embodiments, folding may be achieved using forceps, fingers or tweezers or a combination thereof.

Figure 12:
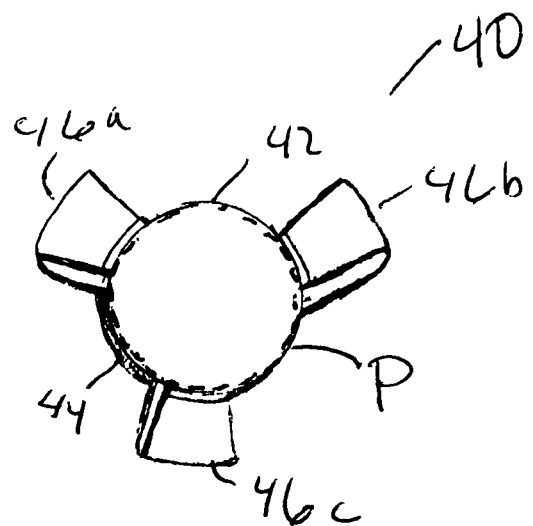
FIGS. 12-14 illustrate a technique for preparing an IOL for loading into an IOL inserter.

In some embodiments, preparing a multielement IOL for insertion includes loading the IOL into an IOL inserter. One example of an IOL suitable for such techniques is the IOL that was discussed above with reference to FIG. 3. As described above, the IOL of FIG. 3 has a plurality of haptics 46 extending between a first lens element 42 and a second lens element 44. As illustrated in FIG. 12, the haptics extend beyond a periphery P of at least one of the first lens element and the second lens element. According to aspects of the present invention it is advantageous to fold at least one of the haptics radially inward while the first lens element and the second lens element are substantially aligned along the optical axis. An advantage of so loading an IOL is to reduce the profile of the IOL for advancement through an injector. Advantages of the present aspect of the invention can be gained by folding at least one of the haptics of the lens.

In FIG. 12-15, two haptics are folded radially inward while the IOL is disposed on a shelf 129 in the staging area 123 of the inserter. In the illustrated embodiment, the haptics are folded such that a portion of the haptics contacts an exterior side of one of the first lens element and the second lens element. An "exterior side of a lens element" is defined herein to be a side of the lens element that faces away from the remaining lens element(s) of the IOL.

FIG. 12 is a plan view of IOL 40 in which IOL 40 is placed on a flat surface with the first lens element 42 disposed on the flat surface and the second lens element 44 above the surface. In FIG. 12, the first lens element and the second lens element are pushed toward one another. Any suitable technique may be used to push the lens elements toward one another. For example, forceps or a finger may be used to apply a force to the anterior lens element.

It should be appreciated that the haptics may be folded (i.e., folded such that a portion of the haptics contacts an exterior side of one of the first lens element and the second lens element) using any suitable technique. According to some techniques, as illustrated, the IOL may be folded while the IOL is disposed on a shelf in the staging area of an inserter. In other examples of techniques, it is advantageous if the haptics are folded while the IOL is disposed on a suitable surface and subsequently transferred to a staging area of an inserter. For example, the haptics may be folded while the IOL is disposed on a table top or on a separate folding apparatus or on portion of the packaging material in which the IOL.

Figure 13:
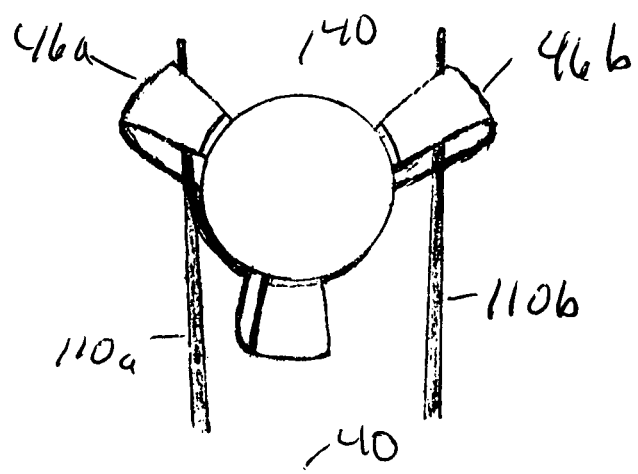

FIG. 13 is a plan view of IOL 40 illustrating that a first arm 110a of a forceps 110 is placed through a first haptic 46a, and a second arm 110b of the forceps 110 is placed through a second haptic 46b.

Figure 14:
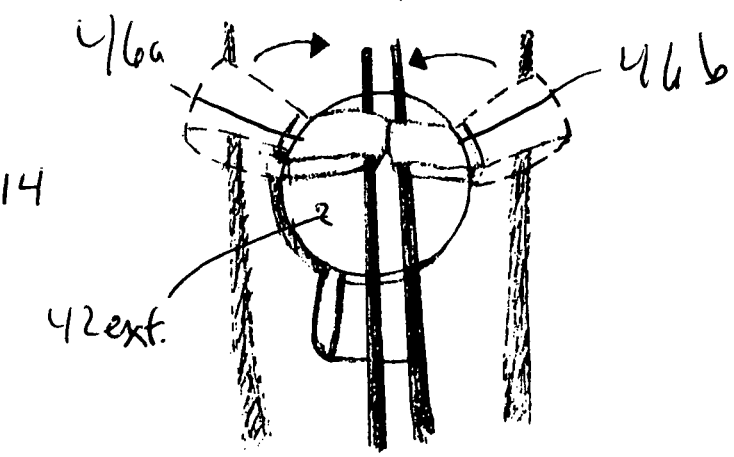

FIG. 14 is a plan view of IOL 40 illustrating folding of the haptics 46a, 46b such that a portion of the haptics contacts an exterior side 42ext of the first lens element 42. Any suitable technique may be used to fold the haptics. For example, forceps or a finger may be used to fold the haptics.

Although separate steps of pushing the lens elements together and folding the haptics are illustrated, it is to be appreciated that such steps may be achieved in a single step. For example, the forceps may be manipulated to fold the IOL such that a portion of the haptics contacts an exterior side of the first lens element while pushing the first lens element toward the second lens element. Also, it is to be appreciated that by moving the haptics, the first lens element will naturally move toward the second lens element another. Further, in some embodiments, the haptics may extend toward the exterior side of the first lens element when the IOL is in an unstressed state (i.e., the first lens element is recessed relative to the haptics) thus facilitating folding the haptics such that a portion of the haptics contacts an exterior side of a lens element, and such that the lens elements are pressed together as the haptics are folded.

Figure 15:
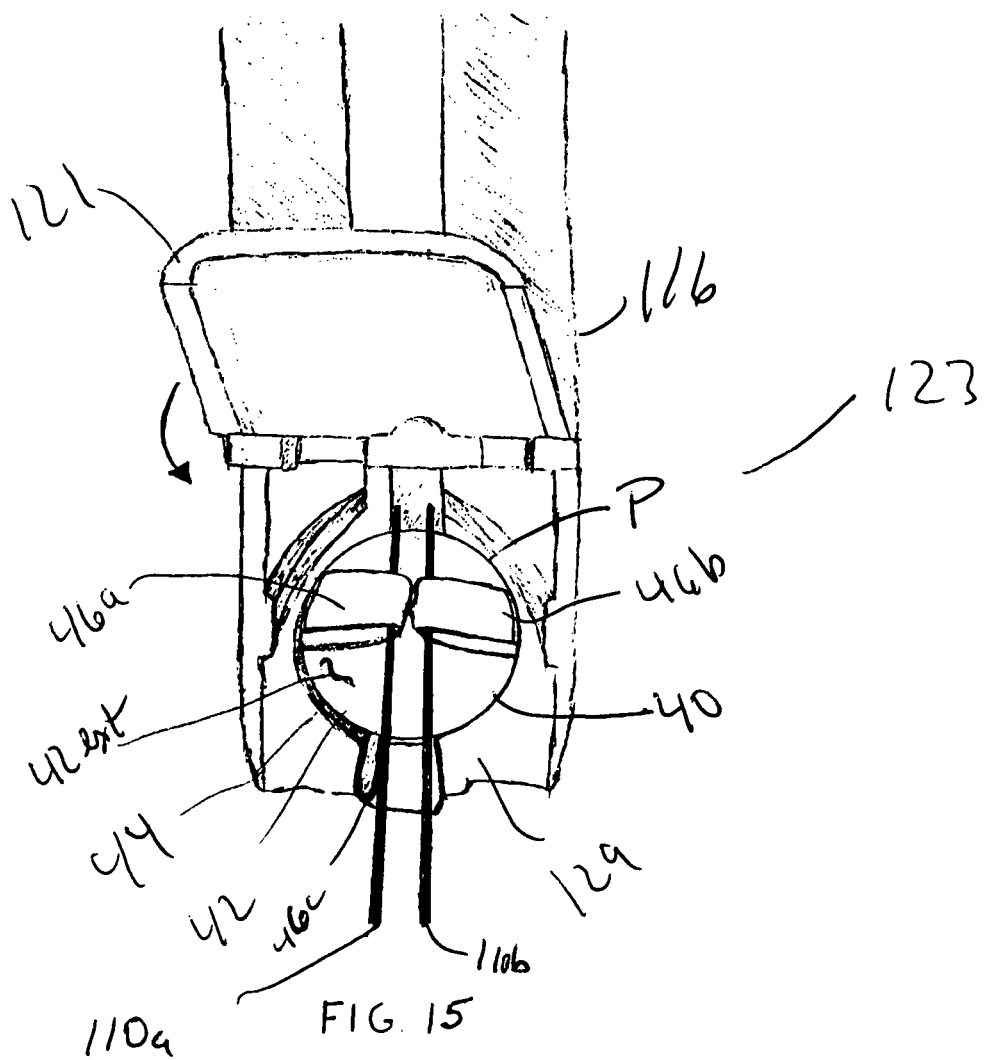
FIG. 15 illustrates locating an IOL onto a staging area of an inserter in which the haptics have been folded in a first configuration.

FIG. 15 is a plan view of the IOL 40 in which second lens element 44 is placed on shelf 129 of an inserter while maintaining the haptics 46a, 46b (e.g., with forceps 110a, 110b) such that a portion of the haptics contacts an exterior side 42ext of the first lens element 42. The third haptic 46c of the IOL is flexed as a result of the first lens element and the second lens element being pushed together but, in some embodiments, is otherwise not folded when placed on the loading deck. The third haptic is oriented so as to extend toward the tip 195 (shown in FIG. 17A) through which the IOL is injected into an eye. Subsequently, the forceps are removed while cover 121 is closed, such that the haptics are maintained in the folded state by the cover as the forceps are removed. The closed cover maintains the haptics such that a portion of the haptics contacts an exterior side of the first lens element. After closing the cover, the plunger of the inserter may be actuated to inject the IOL into the eye.

In some embodiments, haptics 46a and 46b are folded to be substantially entirely within periphery P. However, the invention is not so limited and in some embodiments, the haptics are only partially within the periphery P. Furthermore, although in FIG. 15, only two haptics are illustrated as folded, in other embodiments one or three or more haptics may be so folded.

In some embodiments of the above technique, the first lens element 42 is an anterior lens element of an IOL. In such embodiments, the haptics 46a and 46b contact an anterior side of the anterior lens element (when folded as shown in FIG. 15). For example, in such embodiments, IOL 40 is placed on shelf 129 with the posterior lens element disposed on the surface and the anterior lens element above the surface. Subsequently, the haptics are folded onto the anterior side of the anterior lens element.

In other embodiments, the first lens element 42 is a posterior lens of the IOL. In such embodiments, the haptics 46a, 46b are folded such that a portion of the haptics contacts a posterior side of the posterior lens element. For example, in such embodiments, IOL 40 is placed on shelf 129 with the anterior lens element disposed on the surface and the posterior lens element above the surface. Subsequently, the haptics are folded onto the posterior side of the posterior lens element.

Figure 16:
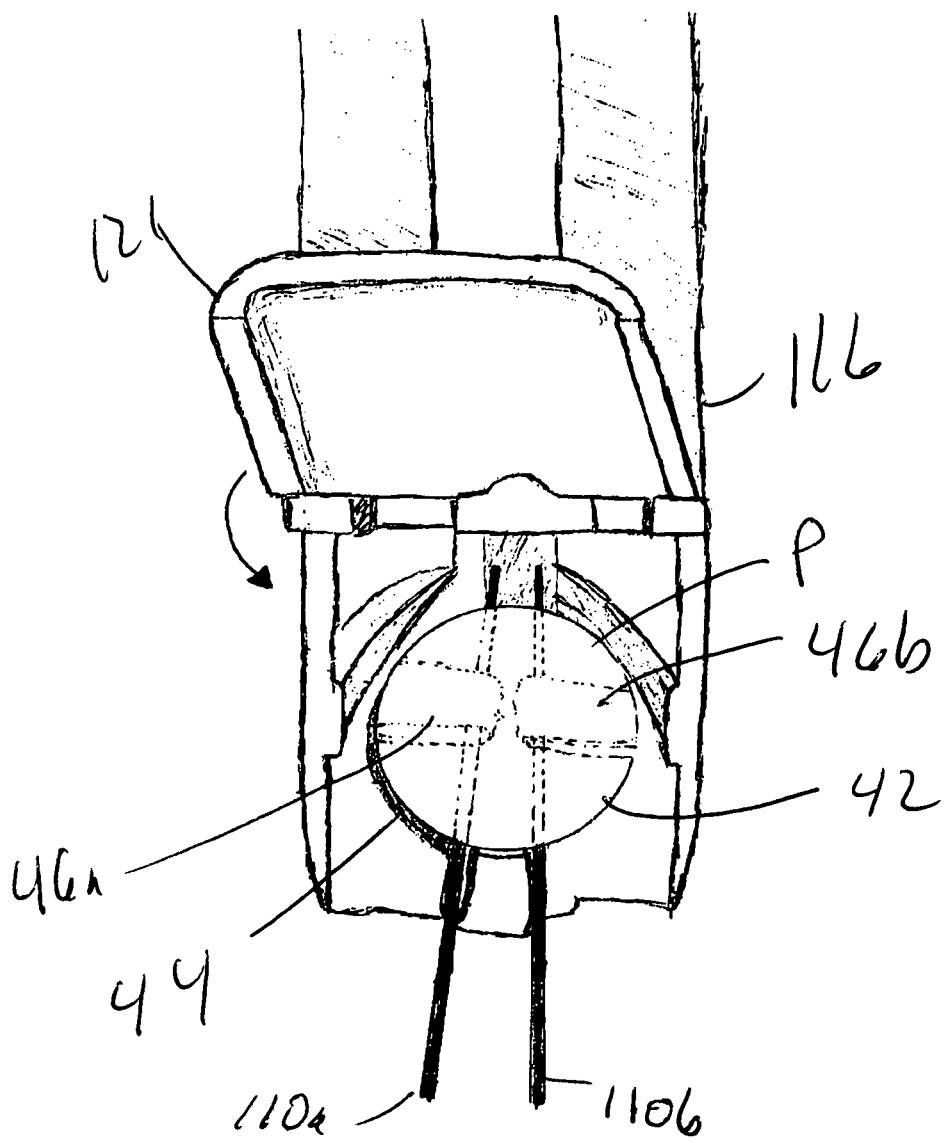
FIG. 16 illustrates locating an IOL onto a staging area of an inserter in which the haptics have been folded in an alternate configuration to FIG. 15.

FIG. 16 illustrates another example of an embodiment of a technique for loading an IOL by folding at least one of the haptics radially inward. In contrast to FIG. 15, which illustrates that the haptics are folded so as to contact an exterior surface of the second lens element, in the embodiment of FIG. 16 illustrates a technique in which haptics 46a, 46b are folded such that they are disposed between the first lens element and the second lens element. After closing the cover, the plunger of the inserter may be actuated to inject the IOL into the eye.

In some embodiments, haptics 46a and 46b are folded to be substantially entirely within periphery P. However, the invention is not so limited and in some embodiments, the haptics are only partially within the periphery P. Furthermore, although in FIG. 16, only two haptics are illustrated as folded, in other embodiments one or three or more haptics may be so folded.

It is to be understood that although the IOL in the embodiments discussed above has three haptics, the aspects of the invention (illustrated in FIGS. 4A-16) are not so limited. The present aspect of the invention may be used with a multielement IOL having two or four or more haptics so as to reduce the profile of the IOL and prepare the IOL for loading into the inserter.

Figure 17B:
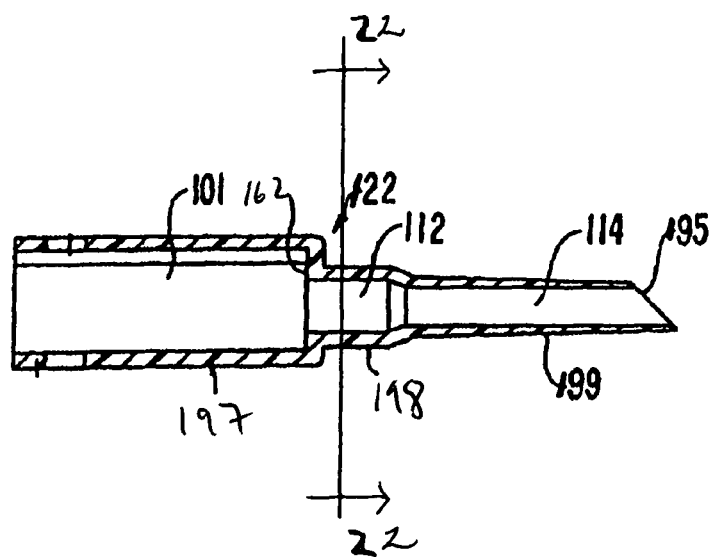

FIGS. 17A and 17B schematically illustrate portions of an embodiment of an inserter 150 having a staging area 123 as illustrated in FIG. 15. One example, of a suitable inserter is the PS30-II produced by Bausch & Lomb, Inc. Portions of the inserter will now be discussed with reference to FIGS. 17A, 17B and 19. The inserter comprises an outer tubular unit 125 and a plunger 118. In one embodiment, tubular unit 125 is formed in part by a proximal member 116 and a distal portion 122 which are coupled together. The components of inserter 150 may be composed of a plastic or metal material. Plunger 118 is actuated to advance an IOL through the tubular unit using a thumb press 119 and finger flanges 141 in a conventional manner.

In the illustrated embodiment, distal portion 122 is subdivided into three graduated sections 197-199. The proximal section 197 has a generally rectangular configuration and defines an inner cavity 101 sized to matingly receive proximal member 116, including cover 121. Section 197 functions to hold cover 121 against shelf segment 129.

The medial section 198 of distal portion 122 is significantly smaller than proximal section 197 so that a rim 162 is defined therebetween. Rim 162 acts as a shoulder in abutment with the aligned distal ends 128, 111 of proximal member 116 and cover 121. The inner wall of medial section 198 converges to define a funnel shaped passage 112. In some embodiments, the funnel portion 112 has an oval cross section, although other shapes could be used. This funnel section causes the lens to become further folded and/or compressed for entry into the eye.

The distal section 199 of distal portion 122 is a long, narrow tube which defines an inner lumen 114. Distal section 199 is to be inserted through the narrow incision made in the eye. As with medial section 198, distal section 199 and lumen 114 may have an oval cross sectional shape. Of course, other shapes could be utilized. To facilitate manufacturing and further compression of an IOL, lumen 114 is formed to taper slightly as it extends forward. Tip 195 of distal portion 122 may be beveled (e.g., at 45 degrees to the longitudinal axis of the inserter lumen) to ease the insertion of the distal portion into the incision and to assist in facilitating a gradual expansion of the lens as it exits from lumen 114. For example, the PS30-II is suitable for inserting an IOL through an incision having a size of 3.0 mm.

Figure 18:
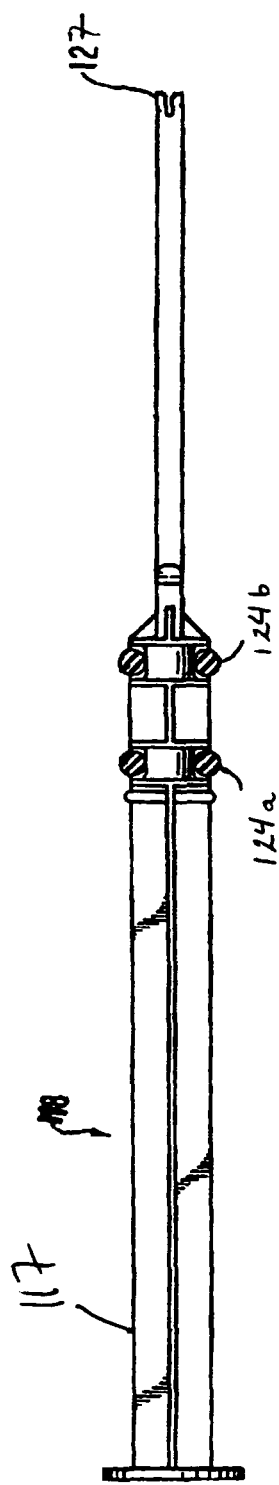
FIG. 18 illustrates an example of a plunger for use in the inserter of FIG. 15.

FIG. 18 illustrates an example of plunger 118 in greater detail. The plunger comprises a main body 117. The forward end of body 117 includes a pair of spaced apart O-rings 124a, 124b. The O-rings provide a level of resistance to enable a more controlled manual operation of the plunger. The O-rings further help to prevent the plunger from inadvertent movement when the surgeon manipulates inserter 150 (shown in FIG. 17A) during the surgical procedure. Other constructions, such as friction fit flanges, could be used in place of the O-ring.

Although FIG. 18 illustrates a plunger tip 127 having a forked shape, in some embodiments, it is advantageous if the tip is flat (i.e., without a fork) to avoid entanglement with the IOL and to provide a relatively large surface area with which to push the IOL. In some embodiments, it may be advantageous that the tip be covered with or made of a soft material such as silicone.

Figure 19:
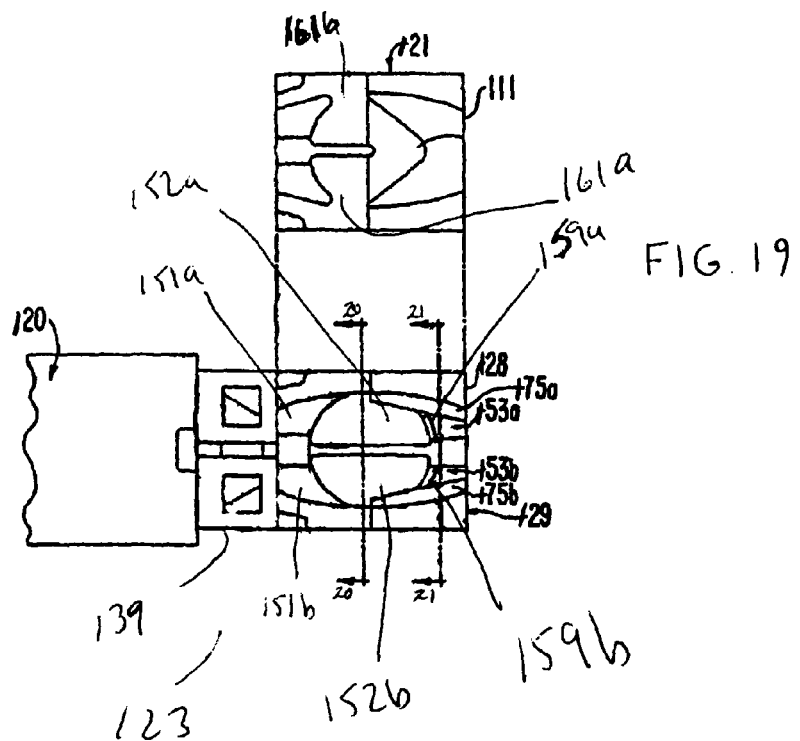
FIG. 19 illustrates further details of the staging area of the inserter of FIG. 15.

Referring to FIG. 19 further details of the staging area will be discussed. In the staging area, shelf segment 129 cooperates with cover 121 to define a staging area compartment 145 for holding an IOL. The interior side of shelf segment 129 is formed in part by a pair of ledges 151a, 151b adjacent neck 139, a pair of recessed central flats 152a, 152b, and a pair of ramps 153a, 153b spaced forwardly of flats 152a, 152b. Ramps 153a, 153b further include sloped surfaces 159a, 159b inclined to flats 152a, 152b. Flats 152a, 152b are recessed relative to top surfaces of ledges 151a, 151b, and ramps 155a, 155b to define a pocket into which is received the second lens element 144 (see FIG. 15).

Figure 20:
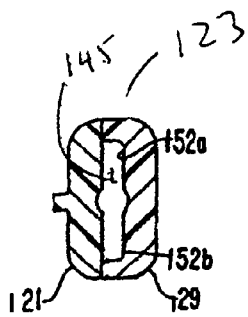
FIG. 20 is a cross-sectional view of the inserter of FIG. 15 taken along line 20-20 of FIG. 19.

FIG. 20 is a cross-sectional view of the inserter in FIG. 17A taken along line 20-20 of FIG. 19 that shows aspects of the staging area in greater detail. Cover 121 lies against shelf segment 129 to form staging area compartment 145 and enclose an IOL with the haptics maintained in a folded state. Cover 121 includes on its interior side recessed sections 161a, 161b, the central portions of which lie opposed to the proximal half of flats 152a, 152b, respectively.

Figure 21:
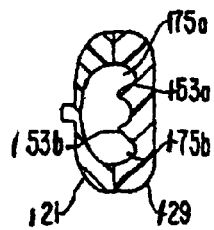
FIG. 21 is a cross-sectional view of the inserter of FIG. 15 taken along line 21-21 of FIG. 19.

FIG. 21 is a cross-sectional view of the inserter in FIG. 17A taken along line 21-21 of FIG. 19 that shows further details of ramps 153a and 153b.

Figure 22:
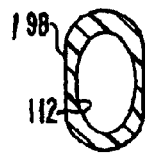
FIG. 22 is a cross-sectional view of the inserter of FIG. 15 taken along line 22-22 of FIG. 17B.

FIG. 22 is a cross-sectional view of the inserter in FIG. 17A taken along line 22-22 of FIG. 17B that shows a cross-section of the lumen of the inserter. Further details of a suitable injector for use with aspects of the present invention are given in U.S. Pat. No. 6,685,740 issued Feb. 3, 2004, to Figueroa, et al. The substance of said patent is hereby incorporated by reference.

Figure 23:
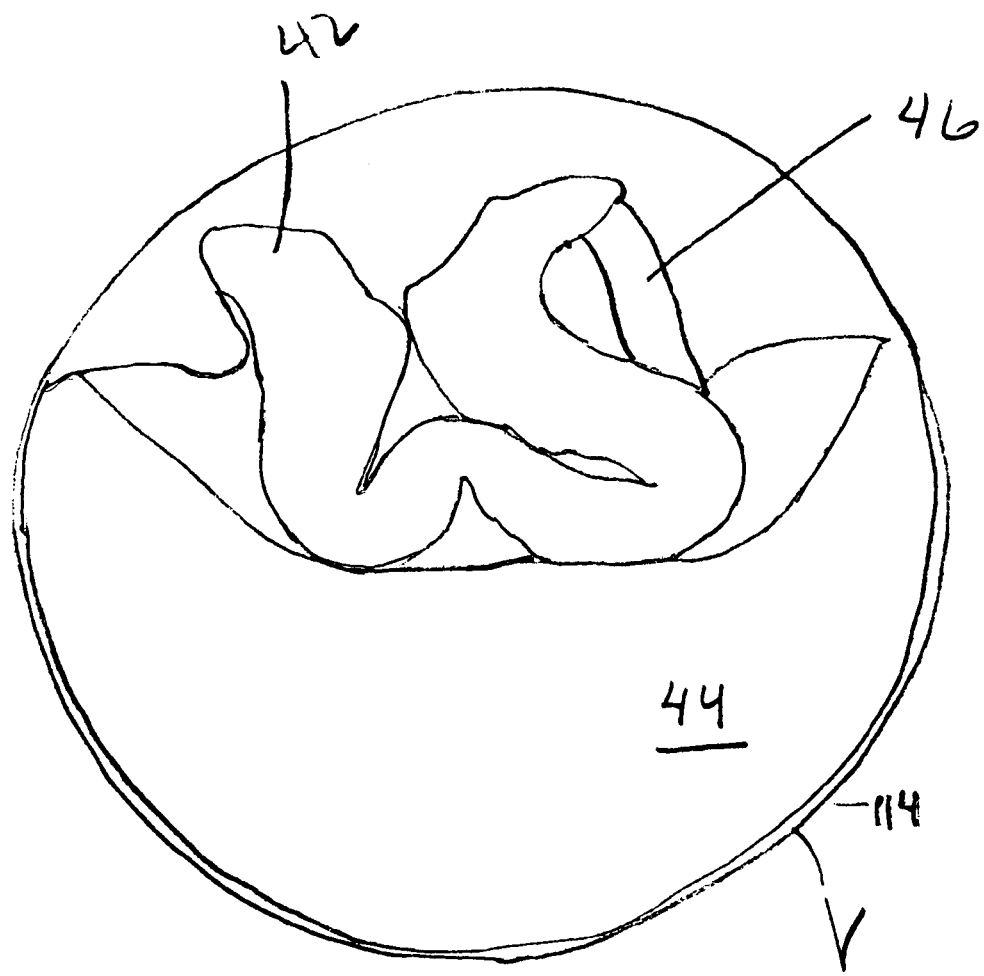
FIG. 23 is a cut away view of an inserter as in FIG. 17A where the inserter is cut away at a location along a lumen, and where an IOL is disposed at the location (both the lumen wall and the lens have been cut away)

FIG. 23 is a cut away view of an IOL 40 at a location along lumen 114 in which both the lumen wall 114 and the IOL have been cut away. FIG. 23 illustrates the configuration of the IOL after the anterior lens element (i.e., second lens element 44) and the posterior lens element (i.e., first lens element 42) have been folded using the technique illustrated in FIGS. 12-15 and the plunger of inserter 150 has been actuated to position the IOL into the lumen of the inserter. FIG. 23 illustrates that the anterior lens of the IOL partially surrounds the posterior lens. Only a first haptic 46 is visible in the cutaway view. It is to be appreciated that, in the illustrated embodiment, the anterior lens has formed a single concavity in which the posterior lens is located. The posterior lens has taken a complex shape corresponding to a "W." According to some techniques, a drop of viscoelastic can be placed on shelf 129 prior to placement of the second lens element on the shelf. Additionally, viscoelastic can be inserted into the distal potion 122 prior to actuation of the plunger. Viscoelastic V is visible between portions of the IOL and portion of the lumen wall 114 in FIG. 23. Additionally, space that is present between the upper portion of wall 114 and lens element 42 may be the result of the process of cutting the IOL and the wall; in an actual device it is believed that the lens will typically fit snuggly with the inside of the lumen wall.

As discussed above, an advantage of this folding technique is that contact between the surfaces of the first lens element and the second lens element is limited; and the folding of the lenses provides substantial potential energy, such that when the IOL is released from its folded (i.e., stressed) state, the first lens element and the second lens element readily separate from one another. That is, they overcome and cohesion between the lenses and readily attain an unstressed state. Viscoelastic assists in separation of the lens elements.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method of folding a multiple element IOL comprising a first optical element and a second optical element that are aligned along an optical axis, the first optical element and second optical element coupled together by two or more haptics, the method comprising:

folding the first optical element and folding the second optical element; wherein the steps of folding the first optical element and folding the second optical element comprise the steps of: (i) folding the first optical element; and (ii) folding the second optical element such that the second optical element at least partially surrounds the first optical element;
wherein after the steps of folding, both the first optical element and the second optical element are substantially aligned along the optical axis; and the first optical element is folded such that radially outer-most portions of the first optical element are displaced towards the second optical element;
wherein the step of folding the first optical element occurs prior to the step of folding the second optical element.

2. The method of claim 1, wherein after said step of folding, the second optical element is configured to form a single concavity in which the first optical element is disposed.

3. The method of claim 1, wherein the step of folding the first optical element comprises folding the first optical element substantially along its centerline.

4. The method of claim 1, wherein the step of folding the second optical element comprises folding the second optical element substantially along its centerline.

5. The method of claim 1, wherein the first optical element is an anterior optical element and the second optical element is a posterior optical element.

6. The method of claim 1, wherein the first optical element is a posterior optical element and the second optical element is an anterior optical element.

7. The method of claim 1, wherein the second optical element is more massive than the first optical element.

8. The method of claim 1, wherein after said step of folding, at least a portion of an interior surface of the second optical element contacts at least a portion of an exterior surface of said first optical element.

9. The method of claim 1, wherein the step of folding the second optical element comprises (1) locating the second optical element on a hinged apparatus, the hinged apparatus comprising a first portion and a second portion, the first portion being connected to the second portion by a hinge; and (2) rotating the first portion relative to the second portion.

10. The method of claim 9, further comprising loading the hinged apparatus into an IOL inserter while maintaining the IOL in the hinged apparatus.

11. The method of claim 10, further comprising actuating the IOL inserter to insert the IOL into an eye.

12. The method of claim 11, wherein the step of actuating the IOL inserter results in compression of the IOL prior to insertion in the eye.

13. The method of claim 1; wherein
the step of folding the first optical element comprises folding the first optical element such that outer portions of the first optical element are displaced towards the second optical element, resulting in said IOL having a folded first optical element; and
the step of folding the second optical element comprises:
(i) locating the second optical element of said IOL that has such folded first optical element on a hinged apparatus having a first portion and a second portion coupled together by a hinge, the hinge extending across the optical axis; and
(ii) with the second optical element so located, rotating the first portion of the hinged apparatus relative to the second portion of the hinted apparatus to cause the second optical element to be folded such that the second optical element at least partially surrounds the first optical element and such that, after folding, both the first optical element and the second optical element are substantially aligned along the optical axis;
wherein said method produces a folded multiple element IOL.

14. The method of claim 13, wherein the first optical element is an anterior optical element and the second optical element is a posterior optical element.

15. The method of claim 13, wherein the first optical element is a posterior optical element and the second optical element is an anterior optical element.

16. The method of claim 13, wherein the second optical element is more massive than the first optical element.

17. The method of claim 13, wherein after said step of rotating, at least a portion of an interior surface of the second optical element contacts at least a portion of an exterior surface of said first optical element.

18. The method of claim 13, further comprising loading the hinged apparatus into an IOL inserter while maintaining such folded multiple element IOL in the hinged apparatus.

19. The method of claim 18, further comprising actuating the IOL inserter to insert the IOL into an eye.

20. The method of claim 18, the step of actuating the IOL inserter results in compression of the IOL prior to insertion in the eye.

21. The method of claim 13, wherein the hinged apparatus comprises a longitudinal axis, wherein the hinge is aligned such that the first portion rotates about an axis parallel to the longitudinal axis.

* * * * *